(12) United States Patent
Zhou et al.

(10) Patent No.: US 8,637,715 B2
(45) Date of Patent: Jan. 28, 2014

(54) CATALYSTS COMPRISING SECONDARY NOBLE METALS AND PROCESS FOR PRODUCING ETHANOL

(75) Inventors: Zhenhua Zhou, Houston, TX (US); Victor Johnston, Houston, TX (US); Heiko Weiner, Pasadena, TX (US); Radmila Wollrab, Pasadena, TX (US)

(73) Assignee: Celanese International Corporation, Irving, TX (US)

( * ) Notice: Subject to any disclaimer, the term of this patent is extended or adjusted under 35 U.S.C. 154(b) by 43 days.

(21) Appl. No.: 13/480,163

(22) Filed: May 24, 2012

(65) Prior Publication Data

US 2013/0165700 A1    Jun. 27, 2013

Related U.S. Application Data

(60) Provisional application No. 61/578,517, filed on Dec. 21, 2011.

(51) Int. Cl.
   *C07C 29/149* (2006.01)
(52) U.S. Cl.
   USPC .......................................................... 568/885
(58) Field of Classification Search
   USPC .......................................................... 568/885
   See application file for complete search history.

(56) References Cited

U.S. PATENT DOCUMENTS

| 4,517,391 | A  | 5/1985  | Schuster et al. |
| 4,777,303 | A  | 10/1988 | Kitson et al. |
| 4,804,791 | A  | 2/1989  | Kitson et al. |
| 5,149,680 | A  | 9/1992  | Kitson et al. |
| 6,204,417 | B1 | 3/2001  | Fischer et al. |
| 6,495,730 | B1 | 12/2002 | Konishi et al. |
| 7,863,489 | B2 | 1/2011  | Johnston et al. |
| 8,080,694 | B2 | 12/2011 | Weiner et al. |
| 2010/0029995 | A1 | 2/2010 | Johnston et al. |
| 2010/0121114 | A1 | 5/2010 | Johnston et al. |
| 2010/0197985 | A1 | 8/2010 | Johnston et al. |
| 2011/0098501 | A1 | 4/2011 | Johnston et al. |
| 2011/0263911 | A1 | 10/2011 | Johnston et al. |
| 2012/0149949 | A1 | 6/2012 | Weiner et al. |
| 2012/0238785 | A1 | 9/2012 | Zhou et al. |

FOREIGN PATENT DOCUMENTS

EP    0175558    3/1986

OTHER PUBLICATIONS

T. Yokoyama, et al., "Carboxylic Acids and Derivatives", Fine Chemicals through Heterogenous Catalysis, pp. 370-379.
International Search Report and Written Opinion mailed on Apr. 25, 2013 in corresponding International Application No. PCT/US2012/070937.

*Primary Examiner* — Elvis O Price

(57) ABSTRACT

The present invention relates to a catalyst comprising platinum, tin and a secondary noble metal selected from the group consisting of rhodium, palladium, gold and iridium. The catalyst may be on a support. In some embodiments, the support may comprise calcium. The catalyst is used for converting acetic acid to ethanol.

21 Claims, No Drawings

US 8,637,715 B2

CATALYSTS COMPRISING SECONDARY NOBLE METALS AND PROCESS FOR PRODUCING ETHANOL

CROSS REFERENCE TO RELATED APPLICATIONS

This claims priority to U.S. Provisional Application No. 61/578,517, filed Dec. 21, 2011, the entire contents and disclosures of which are hereby incorporated by reference.

FIELD OF THE INVENTION

The present invention relates to a catalyst composition comprising platinum, tin and at least one secondary noble metal, wherein the catalyst composition is on a support, preferably comprising calcium. The secondary noble metal is selected from the group consisting of rhodium, palladium, gold and iridium. The present invention also relates to using the catalyst composition for manufacturing ethanol from acetic acid under hydrogenation conditions.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulosic materials, such as corn or sugar cane. Conventional methods for producing ethanol from organic feed stocks, as well as from cellulosic materials, include the acid-catalyzed hydration of ethylene, methanol homologation, direct alcohol synthesis, and Fischer-Tropsch synthesis. Instability in organic feed stock prices contributes to fluctuations in the cost of conventionally produced ethanol, making the need for alternative sources of ethanol production all the greater when feed stock prices rise. Starchy materials, as well as cellulosic materials, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. The reduction of various carboxylic acids over metal oxides has been proposed by EP 0175558 and U.S. Pat. No. 4,398,039. A summary of some of the developmental efforts for hydrogenation catalysts for conversion of various carboxylic acids is provided in Yokoyama, et al., "Carboxylic acids and derivatives" in: *Fine Chemicals Through Heterogeneous Catalysis,* 2001, 370-379.

U.S. Pat. No. 8,080,694, the entire contents and disclosures of which are hereby incorporated by reference, describes a process for hydrogenating alkanoic acids in the present of a catalyst comprising a platinum group metal, a metallic promoter, and a silicaceous support promoted with a redox promoter. U.S. patent application Ser. No. 13/179,955, the entire contents and disclosures of which are hereby incorporated by reference, describes a process for forming ethanol comprising hydrogenating acetic acid in the presence of a catalyst comprising platinum, tin and optionally a third metal on a support. U.S. Pat. No. 7,863,489, the entire contents and disclosures of which are hereby incorporated by reference, describes a process for the formation of ethanol by the hydrogenation of acetic acid in the presence of a catalyst consisting essentially of platinum and tin. U.S. patent application Ser. No. 12/588,727, the entire contents and disclosures of which are hereby incorporated by reference, describes processes for producing ethanol by the hydrogenation of acetic acid in the presence of a catalyst comprising or consisting essential of platinum and tin on a silicaceous support or a modified silicaceous support. U.S. patent application Ser. No. 12/698,947, the entire content and disclosures of which are hereby incorporated by reference, describes a process for producing ethanol by hydrogenating acetic acid in the presence of a catalyst comprising a first metal, a silicaceous support, and at least one support modifier.

U.S. Pat. No. 6,495,730 describes a process for hydrogenating carboxylic acid using a catalyst comprising activated carbon to support active metal species comprising ruthenium and tin. U.S. Pat. No. 6,204,417 describes another process for preparing aliphatic alcohols by hydrogenating aliphatic carboxylic acids or anhydrides or esters thereof or lactones in the presence of a catalyst comprising platinum and rhenium. U.S. Pat. No. 5,149,680 describes a process for the catalytic hydrogenation of carboxylic acids and their anhydrides to alcohols and/or esters in the presence of a catalyst containing a Group VIII metal, such as palladium, a metal capable of alloying with the Group VIII metal, and at least one of the metals rhenium, tungsten or molybdenum. U.S. Pat. No. 4,777,303 describes a process for the productions of alcohols by the hydrogenation of carboxylic acids in the presence of a catalyst that comprises a first component which is either molybdenum or tungsten and a second component which is a noble metal of Group VIII on a high surface area graphitized carbon support. U.S. Pat. No. 4,804,791 describes another process for the production of alcohols by the hydrogenation of carboxylic acids in the presence of a catalyst comprising a noble metal of Group VIII and rhenium. U.S. Pat. No. 4,517,391 describes preparing ethanol by hydrogenating acetic acid under superatmospheric pressure and at elevated temperatures by a process using a predominantly cobalt-containing catalyst.

Existing processes suffer from a variety of issues impeding commercial viability including: (i) catalysts without requisite selectivity to ethanol; (ii) catalysts which are possibly prohibitively expensive and/or nonselective for the formation of ethanol and that produce undesirable by-products; (iii) required operating temperatures and pressures which are excessive; and/or (iv) insufficient catalyst life.

SUMMARY OF THE INVENTION

In a first embodiment, the invention is directed to a process for producing of ethanol comprising: contacting a feed stream containing acetic acid and hydrogen at an elevated temperature with a hydrogenating catalyst comprising platinum, tin, and at least one secondary noble metal on a support material, wherein the secondary noble metal is selected from the group consisting of rhodium, palladium, gold, and iridium. In one preferred embodiment, the support material comprises calcium. The calcium may be present from 0.1 to 50 wt. % and the platinum, tin and secondary noble metal may be present from 0.5 to 25 wt. %. The secondary noble metal may be present from 0.05 to 5 wt. %. The support may comprise a support modifier, wherein the support modifier is selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In other embodiments, the support modifier may be calcium metasilicate. In still other embodiments, the support modifier is selected from the group consisting of $TiO_2$, $ZrO_2$, $Nb_2O_5$, $Ta_2O_5$, $Al_2O_3$, $B_2O_3$, $P_2O_5$, $Sb_2O_3$, $WO_3$, $MoO_3$, $Fe_2O_3$, $Cr_2O_3$, $V_2O_5$, $MnO_2$, $CuO$, $Co_2O_3$, and $Bi_2O_3$. The support material may be present from 25 to 99 wt. % of the catalyst and may comprise a support selected from the group consisting of silica, silica/alumina, calcium metasilicate, pyrogenic silica, high purity silica, carbon, alumina, and mixtures thereof. In some embodiments, the support comprises silica having a surface area from 50 to 600 $m^2/g$ or having a surface area of at least 250 $m^2/g$. Acetic acid conversion may be greater than 30% and acetic acid selectivity to ethanol may be greater than 80%. Hydrogenation may be performed in a vapor phase at a temperature of from 125° C. to 350° C., a pressure of 10 kPa to 3000 kPa, and a hydrogen to acetic acid mole ratio of greater than 4:1. The feed stream may be formed by gasifying a carbonaceous material, wherein the carbonaceous material is oil, coal, natural gas or biomass.

In a second embodiment, the invention is directed to a hydrogenation catalyst for converting acetic acid to ethanol, the catalyst comprising platinum, tin, and at least one secondary noble metal on a support, wherein the secondary noble metal is selected from the group consisting of rhodium, palladium, gold, and iridium. In one preferred embodiment, the support material comprises calcium. The support may comprise from 0.1 to 50 wt. % of a support modifier, wherein the support modifier is selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In other embodiments, the support modifier may be calcium metasilicate. In still other embodiments, the support modifier is selected from the group consisting of $TiO_2$, $ZrO_2$, $Nb_2O_5$, $Ta_2O_5$, $Al_2O_3$, $B_2O_3$, $P_2O_5$, $Sb_2O_3$, $WO_3$, $MoO_3$, $Fe_2O_3$, $Cr_2O_3$, $V_2O_5$, $MnO_2$, $CuO$, $Co_2O_3$, and $Bi_2O_3$. The support material may be present from 25 to 99 wt. % of the catalyst and may comprise a support selected from the group consisting of silica, silica/alumina, calcium metasilicate, pyrogenic silica, high purity silica, carbon, alumina, and mixtures thereof. The support modifier may be present from 0.1 to 50 wt. % and the platinum, tin and secondary noble metal may be present from 0.5 to 25 wt. %.

In a third embodiment, the present invention is directed to a process for producing ethanol comprising contacting a feed stream containing acetic acid and hydrogen at an elevated temperature with a hydrogenating catalyst comprising platinum, tin and rhodium on a support material.

DETAILED DESCRIPTION OF THE INVENTION

Catalyst Composition

The present invention relates to a catalyst composition comprising platinum, tin and a secondary noble metal on a support, preferably a support that comprises calcium. In one embodiment, the secondary noble metal is selected from the group consisting of at least one of rhodium, palladium, gold, iridium, and mixtures thereof. More preferably the secondary noble metal is rhodium. The calcium in the support may be present as an oxide or silicate. Without being bound by theory, the presence of the secondary noble metal may improve the catalyst performance, including acetic acid conversion, ethanol selectivity, and/or productivity. In addition, the secondary noble metal may reduce the metal loading of the active metals, in particular the metal loading of platinum.

The catalyst compositions of the present invention may comprise from 0.1 wt. % to 20 wt. %. platinum, e.g., from 0.2 wt. % to 5 wt. % platinum or from 0.5 wt. % to 2 wt. % platinum. In some embodiments, platinum is present from 0.6 wt. % to 1 wt. %. The catalyst composition may comprise from 0.1 wt. % to 20 wt. % tin, e.g., from 0.2 wt. % to 10 wt. % tin or from 0.5 wt. % to 7.5 wt. % tin. In some embodiments, the tin is present from 1.2 wt. % to 3 wt. %. The secondary noble metal of rhodium, palladium, gold and/or iridium may be present from 0.05 wt. % to 5 wt. %, e.g., from 0.05 wt. % to 2 wt. % or from 0.05 wt. % to 1 wt. %.

The total weight of all the active metals, including secondary noble metal, present in the catalyst preferably is from 0.5 to 25 wt. %, e.g., from 0.5 to 15 wt. %, or from 0.5 wt. % to 10 wt. %. In one embodiment, the active metals are present in an amount of less than 3 wt. %, e.g. less than 2.7 wt. % or less than 2.6 wt. %.

For purposes of the present specification, unless otherwise indicated, weight percent is based on the total weight the catalyst including metal and support. In some embodiments, the catalyst may comprise a weight majority of the tin as compared to the platinum and secondary noble metal. Preferably, the secondary noble metal is less, in terms of total weight, than the platinum or tin.

Support Materials

The catalysts of the present invention may be on any suitable support material. In one embodiment, the support material may be an inorganic oxide. In one embodiment, the support material may be selected from the group consisting of silica, alumina, titania, silica/alumina, calcium metasilicate, pyrogenic silica, high purity silica, zirconia, carbon, zeolites and mixtures thereof. Preferably, the support material comprises silica. In preferred embodiments, the support material is present in an amount from 25 wt. % to 99 wt. %, e.g., from 30 wt. % to 98 wt. % or from 35 wt. % to 95 wt. %.

The surface area of siliceous support material, e.g., silica, preferably is at least about 50 $m^2/g$, e.g., at least about 100 $m^2/g$, at least about 150 $m^2/g$, at least about 200 $m^2/g$ or most preferably at least about 250 $m^2/g$. In terms of ranges, the siliceous support material preferably has a surface area of from 50 to 600 $m^2/g$, e.g., from 100 to 500 $m^2/g$ or from 100 to 300 $m^2/g$. High surface area silica, as used throughout the application, refers to silica having a surface area of at least about 250 $m^2/g$. For purposes of the present specification, surface area refers to BET nitrogen surface area, meaning the surface area as determined by ASTM D6556-04, the entirety of which is incorporated herein by reference.

The siliceous support material also preferably has an average pore diameter of from 5 to 100 nm, e.g., from 5 to 30 nm, from 5 to 25 nm or from about 5 to 10 nm, as determined by mercury intrusion porosimetry, and an average pore volume of from 0.5 to 2.0 $cm^3/g$, e.g., from 0.7 to 1.5 $cm^3/g$ or from about 0.8 to 1.3 $cm^3/g$, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the siliceous support material has a morphology that allows for a packing density from 0.1 to 1.0 $g/cm^3$, e.g., from 0.2 to 0.9 $g/cm^3$ or from 0.3 to 0.8 $g/cm^3$. In terms of size, the silica support material preferably has an average particle size, e.g., meaning the diameter for spherical particles or equivalent spherical diameter for non-spherical particles, from 0.01 to 1.0 cm, e.g., from 0.1 to 0.7 cm or from 0.2 to 0.5 cm. Since the one or more active metal(s) that are disposed on or within the support are generally very small in size, those active metals should not substantially impact the size of the overall catalyst particles. Thus, the above particle sizes generally apply to both the size of the support as well as to the final catalyst particles.

A preferred silica support material is SS61138 High Surface Area (HSA) Silica Catalyst Carrier from Saint-Gobain N or Pro. The Saint-Gobain N or Pro SS61138 silica contains approximately 95 wt. % high surface area silica; a surface area of about 250 m$^2$/g; a median pore diameter of about 12 nm; an average pore volume of about 1.0 cm$^3$/g as measured by mercury intrusion porosimetry and a packing density of about 0.352 g/cm$^3$.

A preferred silica/alumina support material is KA-160 (Sëd Chemie) silica spheres having a nominal diameter of about 5 mm, a density of about 0.562 g/ml, in absorptivity of about 0.583 g H$_2$O/g support, a surface area of about 160 to 175 m$^2$/g, and a pore volume of about 0.68 ml/g.

Other Support Modifiers

The support material may also comprise at support modifier. In some embodiments, the support modifier may comprise the base metal, e.g., calcium or tungsten. A support modifier may adjust the acidity of the support material. In one embodiment, the total weight of the support modifiers are present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

Support modifiers may adjust the acidity of the silicate support material. For example, the acid sites, e.g. Brønsted acid sites, on the silicate support material may be adjusted by the support modifier to favor selectivity to ethanol during the hydrogenation of acetic acid. The acidity of the silicate support material may adjust the number or the availability of Brønsted acid sites on the silicate support material. The silicate support material may also be adjusted by having the support modifier change the pKa of the silicate support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIII metals, aluminum oxides, and mixtures thereof. Acidic support modifiers include those selected from the group consisting of TiO$_2$, ZrO$_2$, Nb$_2$O$_5$, Ta$_2$O$_5$, Al$_2$O$_3$, B$_2$O$_3$, P$_2$O$_5$, and Sb$_2$O$_3$. Additional acidic support modifiers include those selected from the group consisting of TiO$_2$, ZrO$_2$, Nb$_2$O$_5$, Ta$_2$O$_5$, and Al$_2$O$_3$. The acidic modifier may also include those selected from the group consisting of WO$_3$, MoO$_3$, Fe$_2$O$_3$, Cr$_2$O$_3$, V$_2$O$_5$, Nb$_2$O$_5$, MnO$_2$, CuO, Co$_2$O$_3$, and Bi$_2$O$_3$. Preferably the acidic modifier, if present, comprises tungsten.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. The support modifier may be selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate (CaSiO$_3$). Calcium metasilicate may be crystalline or amorphous.

In one preferred embodiment, the catalyst comprises from 0.25 to 1.25 wt. % platinum and 0.25 to 3 wt. % tin. The catalyst also comprises from 0.1 to 0.2 wt. % of a secondary noble metal, preferably rhodium. These preferred active metals are on a silica support. In one exemplary embodiment, the silica support comprises a support modifier such as CaSiO$_3$.

Process to Preparing the Catalyst Compositions

The present invention also relates to processes for making the catalyst. One or more support modifiers, if desired, may also be added to the support by mixing or through impregnation. Powdered materials of the modified supports or a precursor thereto may pelletized, crushed and sieved and added to the support. The use of a solvent, such as water, glacial acetic acid, a strong acid such as hydrochloric acid, nitric acid, or sulfuric acid, or an organic solvent, may be preferred. The resulting mixture may be stirred and added to additional support material using, for example, incipient wetness techniques. Capillary action then draws the additional support material into the pores in the support material. The support containing a support modifier can then be formed by drying to drive off water and any volatile components within the support solution and depositing the support modifier on the support material. Drying may occur, for example, at a temperature of from 50° C. to 300° C., e.g., from 100° C. to 200° C. or about 120° C., optionally for a period of from 1 to 24 hours, e.g., from 3 to 15 hours or from 6 to 12 hours.

Once formed, the modified supports may be shaped into particles having the desired size distribution, e.g., to form particles having an average particle size in the range of from 0.2 to 0.4 cm. The supports may be extruded, pelletized, tabletized, pressed, crushed or sieved to the desired size distribution. Any of the known methods to shape the support materials into desired size distribution can be employed.

In a preferred method of preparing the catalyst, the active metals are impregnated onto the support. A precursor of platinum preferably is used in the metal impregnation step, such as a water soluble compound or water dispersible compound/complex that includes platinum. Depending on the metal precursor employed, the use of a solvent, such as water, glacial acetic acid or an organic solvent, may be preferred. The tin precursor also preferably is impregnated on the support. Further, a precursor of the secondary noble metal may also be impregnated on the support. The order of the platinum, tin, and secondary noble metal precursor may vary and preferably the metals may be co-impregnated.

Impregnation occurs by adding, optionally drop wise, the platinum precursor, the tin precursor and/or the secondary noble metal precursors, preferably in suspension or solution, to the dry support. The resulting mixture may then be heated, e.g., optionally under vacuum, in order to remove the solvent. Additional drying and calcining may then be performed, optionally with ramped heating to form the final catalyst composition. Upon heating and/or the application of vacuum, the metal(s) of the metal precursor(s) preferably decompose into their elemental (or oxide) form. In some cases, the completion of removal of the liquid carrier, e.g., water, may not take place until the catalyst is placed into use and calcined, e.g., subjected to the high temperatures encountered during operation. During the calcination step, or at least during the initial phase of use of the catalyst, such compounds are converted into a catalytically active form of the metal or a catalytically active oxide thereof.

Impregnation of the platinum, tin, and secondary noble metals on the support may occur simultaneously (co-impregnation) or sequentially. In simultaneous impregnation, the precursors are mixed together and added to the support together, followed by drying and calcination to form the final catalyst composition. With simultaneous impregnation, it may be desired to employ a dispersion agent, surfactant, or solubilizing agent, e.g., ammonium oxalate, to facilitate the dispersing or solubilizing of the precursors in the event the precursors are incompatible with the desired solvent, e.g., water.

In sequential impregnation, the tin precursor is first added to the support followed by drying and calcining, and the resulting material is then impregnated with the platinum precursor followed by impregnated with the secondary noble metal precursor, and additional drying and calcining step to form the final catalyst composition. Preferably, the precious metal is added last in the sequential impregnation. Of course, combinations of sequential and simultaneous impregnation may be employed if desired.

Suitable metal precursors include, for example, metal halides, amine solubilized metal hydroxides, metal nitrates or metal oxalates. For example, suitable compounds for platinum precursors include chloroplatinic acid, ammonium chloroplatinate, amine solubilized platinum hydroxide, platinum nitrate, platinum tetra ammonium nitrate, platinum chloride, platinum oxalate, and sodium platinum chloride. Generally, both from the point of view of economics and environmental aspects, aqueous solutions of soluble compounds of platinum are preferred. A particularly preferred precursor to platinum is platinum ammonium nitrate, $Pt(NH_3)_4(NO_4)_2$. Calcining of the solution with the support and active metal may occur, for example, at a temperature of from 250° C. to 800° C., e.g., from 300 to 700° C. or about 500° C., optionally for a period of from 1 to 12 hours, e.g., from 2 to 10 hours, from 4 to 8 hours or about 6 hours.

In one aspect, the secondary noble metal or metal precursor is first added to the support, followed by the platinum and tin metal or metal precursor. Of course the reverse order of addition is also possible. Exemplary precursors for secondary noble metals include metal halides, amine solubilized metal hydroxides, metal nitrates or metal oxalates. As indicated above, in the sequential embodiment, each impregnation step preferably is followed by drying and calcination. In the case of promoted bimetallic catalysts as described above, a sequential impregnation may be used, starting with the addition of the secondary noble metal followed by a second impregnation step involving co-impregnation of Pt and Sn.

As an example, PtSnRh/CaSiO$_3$ on SiO$_2$ may be prepared by mixing CaSiO$_3$ and SiO$_2$ to form a modified support. Rh(NO$_3$)$_3$ is impregnated onto the support and dried. After the secondary noble metal, rhodium is added, there is a co-impregnation with Pt(NH$_3$)$_4$(NO$_4$)$_2$ and Sn(AcO)$_2$. Again, each impregnation step of Pt and Sn may be followed by drying and calcination steps as necessary. In some embodiments, when impregnation of Pt and Sn is sequential, Sn is impregnated first, dried and calcined, followed by the impregnation of Pt. In most cases, the impregnation may be carried out using metal nitrate solutions. However, various other soluble salts, which upon calcination release metal ions, can also be used. Examples of other suitable metal salts for impregnation include, metal acids, such as perrhenic acid solution, metal oxalates, and the like. In those cases where substantially pure ethanol is to be produced, it is generally preferable to use nitrogenous amine and/or nitrate based precursors.

Use of Catalyst to Hydrogenate Acetic Acid

One advantage of catalysts of the present invention is the stability or activity of the catalyst for producing ethanol. Accordingly, it can be appreciated that the catalysts of the present invention are fully capable of being used in commercial scale industrial applications for hydrogenation of acetic acid, particularly in the production of ethanol. In particular, it is possible to achieve such a degree of stability such that catalyst activity will have a rate of productivity decline that is less than 6% per 100 hours of catalyst usage, e.g., less than 3% per 100 hours or less than 1.5% per 100 hours. Preferably, the rate of productivity decline is determined once the catalyst has achieved steady-state conditions.

In one embodiment there is a process for producing ethanol by hydrogenating feedstock comprising compounds selected from the group consisting of acetic acid, ethyl acetate and mixtures thereof in the presence of the catalyst. One particular preferred reaction is to make ethanol from acetic acid. The hydrogenation reaction may be represented as follows:

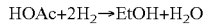

$$HOAc + 2H_2 \rightarrow EtOH + H_2O$$

The raw materials, acetic acid and hydrogen, fed to the primary reactor used in connection with the process of this invention may be derived from any suitable source including natural gas, petroleum, coal, biomass, and so forth. As examples, acetic acid may be produced via methanol carbonylation, acetaldehyde oxidation, ethane oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reactor may also comprise other carboxylic acids and anhydrides, as well as aldehyde and/or ketones, such as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

The reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, from 100 kPa to 2100 kPa or from 200 kPa to 2100 kPa. The reactants may be fed to the reactor at a gas hourly space velocity (GHSV) of greater than 500 hr$^{-1}$, e.g., greater than 1000 hr$^{-1}$, greater than 2500 hr$^{-1}$ or even greater than 5000 hr$^{-1}$. In terms of ranges the GHSV may range from 50 hr$^{-1}$ to 50,000 hr$^{-1}$, e.g., from 500 hr$^{-1}$ to 30,000 hr$^{-1}$, from 1000 hr$^{-1}$ to 10,000 hr$^{-1}$, or from 1000 hr$^{-1}$ to 6500 hr$^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5,000 hr$^{-1}$ or 6,500 hr$^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 8:1. Most preferably, the molar ratio of hydrogen to acetic acid is greater than 2:1, e.g., greater than 4:1 or greater than 8:1. Generally, the reactor may use an excess of hydrogen, while the secondary hydrogenation reactor may use a sufficient amount of hydrogen as necessary to hydrogenate the impurities. In one aspect, a portion of the excess hydrogen from the reactor is directed to the secondary reactor for hydrogenation. In some optional embodiments, the secondary reactor could be operated at a higher pressure than the hydrogenation reactor and a high pressure gas stream comprising hydrogen may be separated from the secondary reactor liquid product in an adiabatic pressure reduction vessel, and the gas stream could be directed to the hydrogenation reactor system.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

In particular, the hydrogenation of acetic acid may achieve favorable conversion of acetic acid and favorable selectivity and productivity to ethanol in the primary reactor. For purposes of the present invention, the term "conversion" refers to the amount of acetic acid in the feed that is converted to a compound other than acetic acid. Conversion is expressed as a percentage based on acetic acid in the feed. The conversion may be at least 30%, e.g., at least 40%, or at least 60%. Although catalysts that have high conversions are desirable, such as at least 60%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. In one embodiment, catalyst selectivity to ethanol is at least 60%, e.g., at least 70%, or at least 80%. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

In various embodiments of the present invention, the crude ethanol product produced by the reactor, before any subsequent processing, such as purification and separation, will typically comprise unreacted acetic acid, ethanol and water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product may comprise acetic acid in an amount less than 20 wt. %, e.g., of less than 15 wt. %, less than 10 wt. % or less than 5 wt. %. In terms of ranges, the acetic acid concentration of Table 1 may range from 0.1 wt. % to 20 wt. %, e.g., 0.2 wt. % to 15 wt. %, from 0.5 wt. % to 10 wt. % or from 1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

An ethanol product may be recovered from the crude ethanol product produced by the reactor using the catalyst of the present invention may be recovered using several different techniques.

The ethanol product may be an industrial grade ethanol comprising from 75 to 96 wt. % ethanol, e.g., from 80 to 96 wt. % or from 85 to 96 wt. % ethanol, based on the total weight of the ethanol product. In some embodiments, when further water separation is used, the ethanol product preferably contains ethanol in an amount that is greater than 97 wt. %, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst, such as zeolite catalysts or phosphotungstic acid calaysts, can be employed to dehydrate ethanol, as described in copending U.S. Pub. Nos. 2010/0030002 and 2010/0030001 and WO2010146332, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

The following examples describe the catalyst and process of this invention.

EXAMPLES

Catalyst Examples A to E

The catalyst supports for the examples are dried at 120° C. overnight under circulating air prior to use. All $SiO_2$ support materials are used as a 14/30 mesh or in original shape (1/16 inch or 1/8 inch pellets) unless mentioned otherwise.

In some examples, powdered materials (i.e., $CaSiO_3$ and/or $WO_3$) are pelletized, crushed and sieved after being added to the support. When $CaSiO_3$ is added to the support, first, an aqueous suspension of $CaSiO_3$ (≤200 mesh) is prepared by adding 0.52 g of the solid to 13 ml of deionized water, followed by the addition of 1.0 ml of colloidal $SiO_2$ (15 wt. % solution, NALCO). The suspension is stirred for 2 hours at room temperature and then added to 10.0 g of $SiO_2$ support (14/30 mesh) using incipient wetness technique. After standing for 2 hours, the material is evaporated to dryness, followed by drying at 120° C. overnight under circulating air and calcination at 500° C. for 6 hours.

Initially, a precursor to the secondary noble metal, e.g. $Rh(NO_3)_3$ (from Heraeus) is dissolved in water and added drop wise to the modified support. Active metals are added to the supports after the support modifier is added. $Pt(NH_3)_4(NO_3)_2$ (from Aldrich) and $Sn(OAc)_2$ (tin acetate, $Sn(OAc)_2$ from Aldrich) is added followed sequentially by adding $Pt(NH_3)_4(NO_3)_2$ to form the Pt/Sn/secondary noble metal-containing Catalysts A-E. In each instance, the metal compound is placed in a vile containing diluted glacial acetic acid (from Fisher), stirred at room temperature for 15 minutes, and then added drop wise to the support material in a 100 ml round-bottomed flask. The metal solution is stirred continuously until all of the metal mixture has been added to the support while rotating the flask after every addition of metal solution. After completing the addition of the metal solution, the flask containing the impregnated catalyst is left standing at room temperature for two hours. The flask is then attached to a rotor evaporator (bath temperature at 80° C.), and evacuated until dried while slowly rotating the flask. The material is then dried further overnight at 120° C., and then calcined using the following temperature program: 25→160° C./ramp 5.0 deg/min; hold for 2.0 hours; 160→500° C./ramp 2.0 deg/min; hold for 4 hours.

Table 2 summarizes the catalysts prepared. The support modifier was present in an amount of 10 wt. %. Catalyst E, comprising Ruthenium as a secondary noble metal, is presented as a comparative example.

TABLE 2

SUPPORT MODIFIED CATALYSTS

| Catalyst | Support with Support Modifier | First Metal (%) | Second Metal (%) | Secondary noble Metal |
|---|---|---|---|---|
| A | $CaSiO_3/SiO_2$ | Pt (0.6 wt. %) | Sn (1.48 wt. %) | Rh |
| B | $CaSiO_3/SiO_2$ | Pt (0.6 wt. %) | Sn (1.48 wt. %) | Pd |
| C | $CaSiO_3/SiO_2$ | Pt (0.6 wt. %) | Sn (1.48 wt. %) | Au |
| D | $CaSiO_3/SiO_2$ | Pt (0.6 wt. %) | Sn (1.48 wt. %) | Ir |
| E | $CaSiO_3/SiO_2$ | Pt (0.6 wt. %) | Sn (1.48 wt. %) | Ru |

Catalysts A through E are placed in separate reactor vessels and dried by heating at 120° C. Feedstock acetic acid vapor is then charged to the reactor vessels along with hydrogen and helium as a carrier gas with an average combined gas hourly space velocity (GHSV) of 2430 $hr^{-1}$, temperature of 250° C., pressure of 2500 kPa, and mole ratio of hydrogen to acetic acid of 8:1. Product samples are taken and analyzed to determine conversion and selectivity. Analysis of the products is carried out by online GC. A three channel compact GC equipped with one flame ionization detector (FID) and 2 thermal conducting detectors (TCD) is used to analyze the feedstock reactant and reaction products. The front channel is equipped with an FID and a CP-Sil 5 (20 m)+WaxFFap (5 m) column and is used to quantify: acetaldehyde; ethanol; acetone; methyl acetate; vinyl acetate; ethyl acetate; acetic acid; ethylene glycol diacetate; ethylene glycol; ethylidene diacetate; and paraldehyde. The middle channel is equipped with a TCD and Porabond Q column and is used to quantify: $CO_2$; ethylene; and ethane. The back channel is equipped with a TCD and molecular sieve 5A column and is used to quantify: helium; hydrogen; nitrogen; methane; and carbon monoxide.

Table 3 summarizes the conversion of acetic acid and selectivity to ethanol for each of Catalysts A to E at 20, 40 and 60 hours. As can be seen, comparative catalyst E begins to deactivate at 60 hours.

TABLE 3

ACETIC ACID CONVERSION AND ETHANOL SELECTIVITY FOR CATALYSTS A TO E

| | Acetic Acid Conversion (%) | | | Ethanol Selectivity (%) | | |
|---|---|---|---|---|---|---|
| Catalyst | 20 hours | 40 hours | 60 hours | 20 hours | 40 hours | 60 hours |
| A | 50% | 66% | 65% | 88% | 89% | 90% |
| B | 38% | 57% | 60% | 88% | 89% | 90% |
| C | 27% | 30% | 31% | 88% | 89% | 87% |

TABLE 3-continued

ACETIC ACID CONVERSION AND ETHANOL
SELECTIVITY FOR CATALYSTS A TO E

| Catalyst | Acetic Acid Conversion (%) | | | Ethanol Selectivity (%) | | |
|---|---|---|---|---|---|---|
| | 20 hours | 40 hours | 60 hours | 20 hours | 40 hours | 60 hours |
| D | 45% | 49% | 47% | 87% | 89% | 89% |
| E | 46% | 47% | 43% | 86% | 89% | 87% |

While the invention has been described in detail, modifications within the spirit and scope of the invention will be readily apparent to those skilled in the art. All publications and references discussed above are incorporated herein by reference. In addition, it should be understood that aspects of the invention and portions of various embodiments and various features recited may be combined or interchanged either in whole or in part. In the foregoing descriptions of the various embodiments, those embodiments which refer to another embodiment may be appropriately combined with other embodiments as will be appreciated by one skilled in the art. Furthermore, those skilled in the art will appreciate that the foregoing description is by way of example only, and is not intended to limit the invention.

We claim:

1. A process for producing of ethanol comprising: contacting a feed stream containing acetic acid and hydrogen at an elevated temperature with a hydrogenating catalyst comprising platinum, tin, and at least one secondary noble metal on a support material, wherein the secondary noble metal is present in an amount less than the amount of the platinum or tin and is selected from the group consisting of rhodium, palladium, gold and iridium; wherein the support material further comprises a support modifier selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof.

2. The process of claim 1, wherein the secondary noble metal is present in an amount from 0.05 to 5 wt. %.

3. The process of claim 1, wherein the support modifier is calcium metasilicate.

4. The process of claim 1, wherein the support material further comprises a support selected from the group consisting of silica, silica/alumina, calcium metasilicate, pyrogenic silica, high purity silica, carbon, alumina, and mixtures thereof.

5. The process of claim 1, wherein acetic acid conversion is greater than 30%.

6. The process of claim 1, wherein acetic acid selectivity to ethanol is greater than 80%.

7. The process of claim 1, wherein the hydrogenation is performed in a vapor phase at a temperature of from 125° C. to 350° C., a pressure of 10 kPa to 3000 kPa, and a hydrogen to acetic acid mole ratio of greater than 4:1.

8. The process of claim 1, wherein the support material comprises silica having a surface area from 50 to 600 m²/g.

9. The process of claim 1, wherein the support material comprises silica having a surface area of at least 250 m²/g.

10. The process of claim 1, further comprising gasifying a carbonaceous material to produce the feed stream.

11. The process of claim 10, wherein the carbonaceous material is selected from the group consisting of oil, coal, natural gas and biomass.

12. The process of claim 1, wherein the support material is present in an amount from 25 wt. % to 99 wt. %, based on the total weight of the catalyst.

13. The process of claim 1, wherein the support modifier is present in an amount from 0.1 wt. % to 50 wt. %, based on the total weight of the catalyst.

14. The process of claim 1, wherein the platinum, tin and secondary noble metal are present in an amount from amount of 0.5 wt. % to 25 wt. %, based on the total weight of the catalyst.

15. A hydrogenation catalyst for converting acetic acid to ethanol, the catalyst comprising platinum, tin, and at least one secondary noble metal on a support material, wherein the secondary noble metal is present in an amount less than the amount of the platinum or tin and is selected from the group consisting of rhodium, palladium, gold, and iridium; wherein the support further comprises a support modifier selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof.

16. The catalyst of claim 15, wherein the support modifier is calcium metasilicate.

17. The catalyst of claim 15, wherein the support material further comprises a support selected from the group consisting of silica, silica/alumina, calcium metasilicate, pyrogenic silica, high purity silica, carbon, alumina, and mixtures thereof.

18. The catalyst of claim 15, wherein the support material is present in an amount from 25 wt. % to 99 wt. %, based on the total weight of the catalyst.

19. The catalyst of claim 15, wherein the support modifier is present in an amount from 0.1 wt. % to 50 wt. %, based on the total weight of the catalyst.

20. The catalyst of claim 15, wherein the platinum, tin and secondary noble metal are present in an amount from amount of 0.5 wt. % to 25 wt. %, based on the total weight of the catalyst.

21. A process for producing ethanol comprising: contacting a feed stream containing acetic acid and hydrogen at an elevated temperature with a hydrogenating catalyst comprising platinum, tin, and rhodium on a support material; wherein the rhodium is present in an amount less than the amount of the platinum or tin and wherein the support further comprises a support modifier selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof.

* * * * *